(12) United States Patent
Eaton et al.

(10) Patent No.: US 7,066,179 B2
(45) Date of Patent: Jun. 27, 2006

(54) PATIENT INTERFACE AND HEADGEAR CONNECTOR

(75) Inventors: Jason P Eaton, Monroeville, PA (US); Peter Ho, Pittsburgh, PA (US); Elias G Diacopoulos, Export, PA (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 10/629,366

(22) Filed: Jul. 29, 2003

(65) Prior Publication Data

US 2004/0025883 A1 Feb. 12, 2004

Related U.S. Application Data

(60) Provisional application No. 60/402,335, filed on Aug. 9, 2002.

(51) Int. Cl.
*A62B 18/08* (2006.01)
*A62B 9/04* (2006.01)
*A61M 16/00* (2006.01)

(52) U.S. Cl. .......................... 128/206.27; 128/206.24; 128/207.11; 128/207.17; 128/DIG. 26; 128/202.27

(58) Field of Classification Search ........... 128/202.27, 128/206.27, 207.11, 207.17, DIG. 26, 205.25, 128/201.24; 24/265 AC, 265 R, 662, 630, 24/686, 265 BC
See application file for complete search history.

(56) References Cited

U.S. PATENT DOCUMENTS

| 1,310,119 A | * | 7/1919 | Harper | 24/662 |
|---|---|---|---|---|
| 2,097,676 A | | 11/1937 | Shindel et al. | |
| 2,375,147 A | * | 5/1945 | Teague | 128/207.11 |
| 3,433,222 A | * | 3/1969 | Pinto | 128/201.24 |
| 3,441,020 A | * | 4/1969 | Aasen et al. | 128/205.25 |
| 3,550,588 A | * | 12/1970 | Stahl | 128/201.15 |
| 4,414,973 A | * | 11/1983 | Matheson et al. | 128/206.15 |
| 4,437,462 A | | 3/1984 | Piljay et al. | |
| 4,960,121 A | * | 10/1990 | Nelson et al. | 128/206.24 |
| 5,069,205 A | * | 12/1991 | Urso | 128/206.21 |
| 5,086,768 A | * | 2/1992 | Niemeyer | 128/205.24 |
| 5,502,878 A | * | 4/1996 | Anscher | 24/265 H |
| 5,517,986 A | | 5/1996 | Starr et al. | |
| 5,555,569 A | * | 9/1996 | Lane | 2/424 |
| 5,662,101 A | | 9/1997 | Ogden et al. | |
| 5,771,886 A | * | 6/1998 | Maire et al. | 128/207.11 |
| 5,924,420 A | * | 7/1999 | Reischel et al. | 128/206.21 |
| 6,192,886 B1 | * | 2/2001 | Rudolph | 128/207.13 |
| 6,374,826 B1 | * | 4/2002 | Gunaratnam et al. | 128/206.21 |
| 6,578,572 B1 | * | 6/2003 | Tischer et al. | 128/201.25 |
| 6,691,314 B1 | * | 2/2004 | Grilliot et al. | 2/5 |
| 2003/0196662 A1 | * | 10/2003 | Ging et al. | 128/204.15 |

FOREIGN PATENT DOCUMENTS

EP 0958841 11/1999
WO WO 00/78383 12/2000

* cited by examiner

*Primary Examiner*—Henry Bennett
*Assistant Examiner*—Andrew Bunin
(74) *Attorney, Agent, or Firm*—Timothy A. Nathan; Michael W. Hass

(57) ABSTRACT

A connection device for connecting a headgear and a mask and a system for supplying a flow of gas to a patient that incorporates such a connection device. The connection device allows independent rotation of each of two independently disconnecting headgear connectors. The gas delivery mask includes a shell, a first connector associated with the shell, a second connector connected to a headgear and realeasably and rotateably connected to the first connector.

45 Claims, 8 Drawing Sheets

PATIENT INTERFACE AND HEADGEAR CONNECTOR

CROSS-REFERENCE TO RELATED APPLICATIONS

This application claims priority under 35 U.S.C. § 119(e) from provisional U.S. patent application No. 60/402,335 filed Aug. 9, 2002, the contents of which are incorporated herein by reference.

BACKGROUND OF THE INVENTION

1. Field of the Invention

The present invention generally relates to a device in a patient interface assembly that connects a headgear and a patient interface device, such as a mask, and to a system for supplying a flow of gas to a patient that incorporates such a connection device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle or the patient's condition, to treat a medical disorder, such as sleep apnea syndrome, in particular, obstructive sleep apnea (OSA), cheynes-stokes respiration, or congestive heart failure.

Non-invasive ventilation and pressure support therapies involve the placement of a patient interface device, which is typically a nasal or nasal/oral mask, on the face of a patient to interface the ventilator or pressure support device with the airway of the patient so that a flow of breathing gas can be delivered from the pressure/flow generating device to the airway of the patient. It is known to maintain such masks on the face of a patient by means of a headgear worn on the patient's head. A typical headgear assembly includes upper and lower straps, each having opposite ends that thread through connecting elements provided on the opposite sides of the mask. Because such masks are typically worn for an extended period of time, it is important the headgear maintain the mask in a tight enough seal against a patient's face without discomfort.

One such headgear is disclosed in U.S. Pat. No. 5,517, 986. The headgear includes a cap-like headpiece adapted to fit the crown and back of a patient's head. Lower straps provide a two-point connection with a gas delivery mask. Additionally, a pair of upper straps can be used to provide a four-point connection with the gas delivery mask if needed. In order to secure the mask in place on a patient's head, each strap passes through an elongated opening on the mask and then bends back on itself to hold in place with hook and loop material. The patient adjusts the length of material that passes through the opening to secure a good fit of the mask. However, if the mask is removed, the adjustment process must be repeated.

Another known mask and headgear connector arrangement is disclosed in International Publication No. WO 00/78383 A1 ("the '383 application"). In this arrangement, a respiratory mask has a rigid frame having a first and second female connectors integrally molded thereto. The female connectors receive male connectors connected to the headgear straps. The female connectors are locked into a single discrete location when engaged. Because the connectors do not swivel independently, the user must take care to ensure that each strap is not twisted when the connectors are engaged. If a strap does become twisted, the user must disconnect the male connectors, straighten the strap and reconnect the male connectors, otherwise the twist of the strap may dislodge the mask from the user, cause the strap to uncomfortably impinge on the user's face, or both.

Published European patent application publication no. EP 0958841 A2 (application no. 99108650.5) discloses a mask and headgear connection assembly that is similar in function to that disclosed in the '383 application. In the European application, loops are provided at the end of the headgear straps and corresponding hooks are provided on the mask shell. This configuration allows the user the easily detach the headgear straps from the mask by removing the loops from the hooks. However, this hook and loop configuration suffers from the same disadvantage as that of the '383 application. Namely, it does not allow the connectors to swivel independently so that twisting of the headgear straps can deteriorate the usefulness of the mask.

SUMMARY OF THE INVENTION

Accordingly, it is an object of the present invention to provide a connection assembly for coupling a patient interface device and a headgear that overcomes the shortcomings of conventional mask/headgear connectors.

An exemplary embodiment of the present invention allows independent rotation of each of two independently disconnecting headgear connectors. The connector allows the user to straighten the headgear straps once the connection to the mask has been made. It does not require any manipulation of the headgear straps around a holding feature, and does not require disconnection of the hook and loop fasteners on the headgear strap to straighten out the headgear straps. An advantage exists therefore as the user may untwist the headgear straps with the mask already held in place. The user does not have to untwist the straps while holding the mask to the face.

An exemplary embodiment of the present invention also aligns the connectors with the direction of the strap pull, thus allowing headgear straps to attach to the mask at the most natural angle for any given individual. It allows easy disconnection and connection of straps. It also allows separation of mask and headgear for cleaning purposes.

An exemplary embodiment of the present invention further comprises an assembly including a headgear having a connection device and a gas delivery mask, and to a system for supplying a flow of gas to a patient that incorporates such a mask and headgear.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

FIGS. 1–4 illustrate an exemplary embodiment of a patient interface assembly 8 including a gas delivery mask 10 and a headgear assembly 11 according to the principles to the present invention. More specifically, these figures illustrate a gas delivery mask 10, which functions as a patient interface device to communicate a flow of breathing gas between a patient's airway and a pressure generating device 12. Examples of pressure generating devices include a ventilator, CPAP device, or variable pressure device, e.g. an auto-tritrating CPAP device or a BiPAP® device manufactured and distributed by Respironics, Inc. of Pittsburgh, Pa., in which the pressure provided to the patient varies with the patient's respiratory cycle so that a higher pressure is delivered during inspiration than during expiration.

Figure 1:
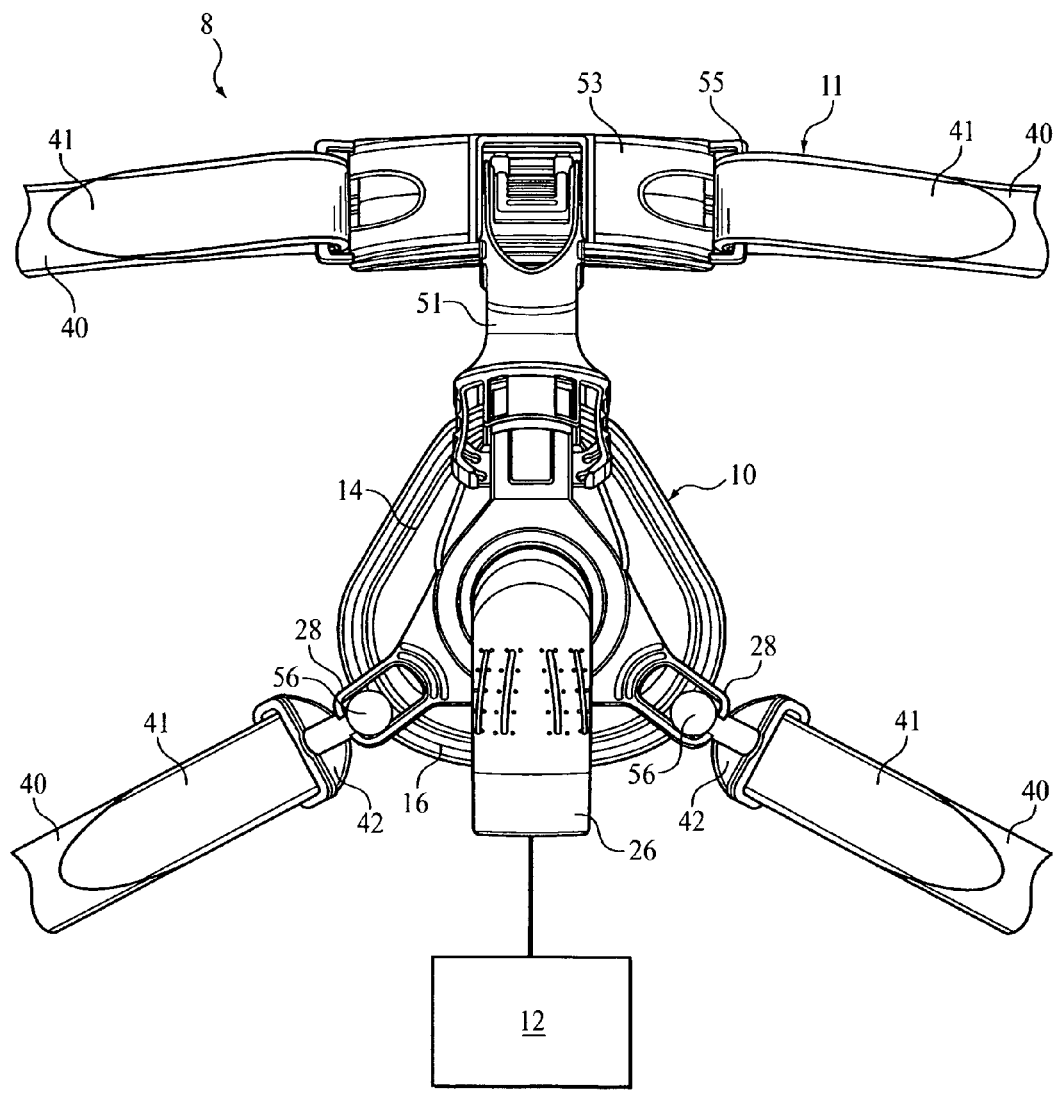
FIG. 1 is a front view of the patient interface assembly according to the principles of an exemplary embodiment of the present invention shown (schematically) connected to a gas flow generating device.
Figure 2:
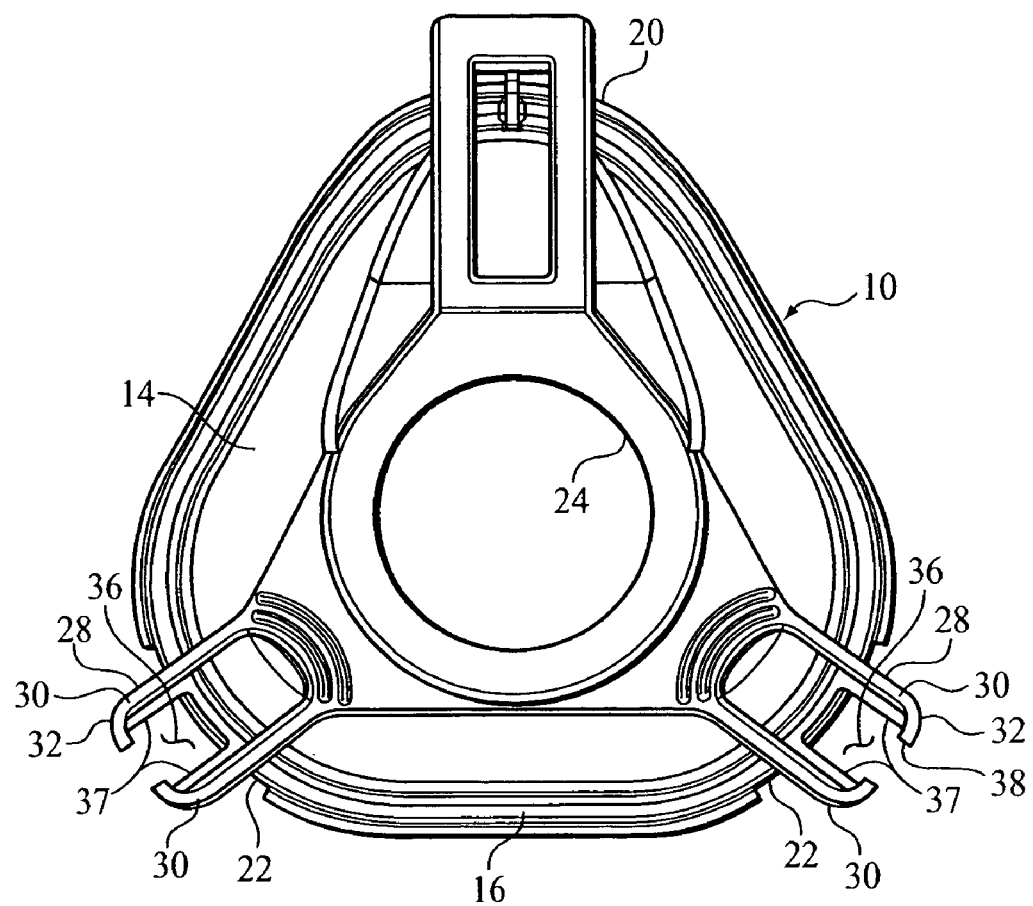
FIG. 2 is a front view of the mask shell in the patient interface assembly of FIG. 1.
Figure 3:
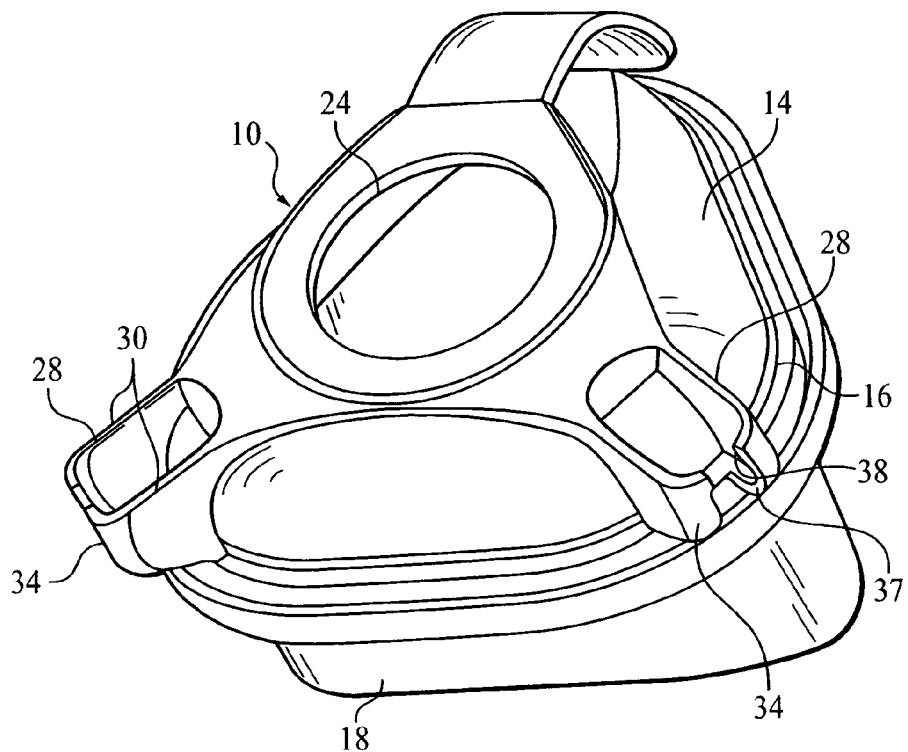
FIG. 3 is a perspective view of the mask shell in the patient interface assembly of FIG. 1.

Referring to FIGS. 1–3, there is illustrated a gas delivery mask 10 including a mask shell 14 or body portion that is preferably, but not necessarily, a generally rigid structural shell having an open side that defines an annular portion 16 to which a resilient, relatively soft seal member 18 or cushion is attached. In the illustrated exemplary embodiment, mask shell 14 is substantially triangular in shape, having an upper apex angle 20 and two lower angles 22. Mask shell 14 includes an inlet opening 24 adapted to receive a gas supply conduit 26. Seal member 18 is configured to receive a portion of the patient, such as the nose. Alternatively, mask 10 may, instead, comprise a nasal/oral mask configured to enclose the nose and mouth of a patient, or an oral mask configured to enclose only the mouth of a patient. Seal 18 defines the portion of the mask that contacts the user.

In the illustrated exemplary embodiment, a pair of first connectors 28 are rigidly attached to lower angles 22 of mask shell 14. Each first connector 28 includes relatively thin parallel walls 30, as perhaps best shown in FIG. 2, that project from lower angles 22 of the shell past annular portion 16. At distal ends 32 of the parallel walls, a notched wall 34 abuts the parallel walls and curves downward toward the annular portion 16 at lower angle 22 of mask shell 14. This is best shown in FIG. 3. Notched wall 34 includes a notch 36 or slot, extending throughout the length of the notched wall, having substantially parallel walls 37 and a small area 38 of reduced width near an upper edge of parallel walls 37.

Headgear straps 40 in headgear assembly 11 are selectively connected to mask 10 by means of a second connector 42. In the illustrated embodiment, a pair of second connectors 42, which are also referred to as strap connectors, are removeably connectable to end portions of headgear straps 40 and are also removeably connectable to first connectors 28 on each side of shell 14. The present invention contemplates that headgear assembly 11 can be any suitable headgear, i.e., and conventional headgear used in the patient interface field. For example, a typical headgear assembly comprises a headpiece (not shown) that overlies a portion of the patient's crania and headgear straps 42 extending therefrom to adjustably connect the headgear to the mask.

Figure 4:
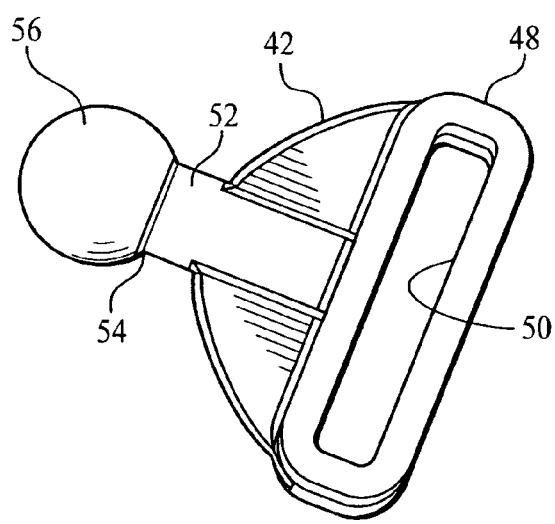
FIG. 4 is a perspective view of a strap connector in the patient interface assembly of FIG. 1 according to the principles of an exemplary embodiment of the present invention.

Each strap connector 42, as best seen in FIG. 4, includes an elongated portion 48 having an elongated opening 50. In a preferred embodiment, elongated portion 48 is rigid. However, the present invention also contemplates that portion 48 can be formed from a pliable or flexible material. In the illustrated embodiment, an end potion 41 of headgear strap 40 is threaded through elongated opening 50 and then bent back on itself to adhere hook and loop elements on the headgear strap connector 42. It is to be understood however, that any conventional technique for securing the end portion of the headgear strap to itself, such as a snap, buckle, or locking clamp, is contemplated by the present invention. In addition, the present invention contemplates a more permanent attachment of the end portion of the headgear strap to strap connector 42. For example, once the patient/user has set the headgear strap to the desired length and threaded in through opening 50, the free end of the strap can be permanently fixed back onto the strap, such as by gluing, sewing, or riveting the overlapping straps together.

Figure 5:
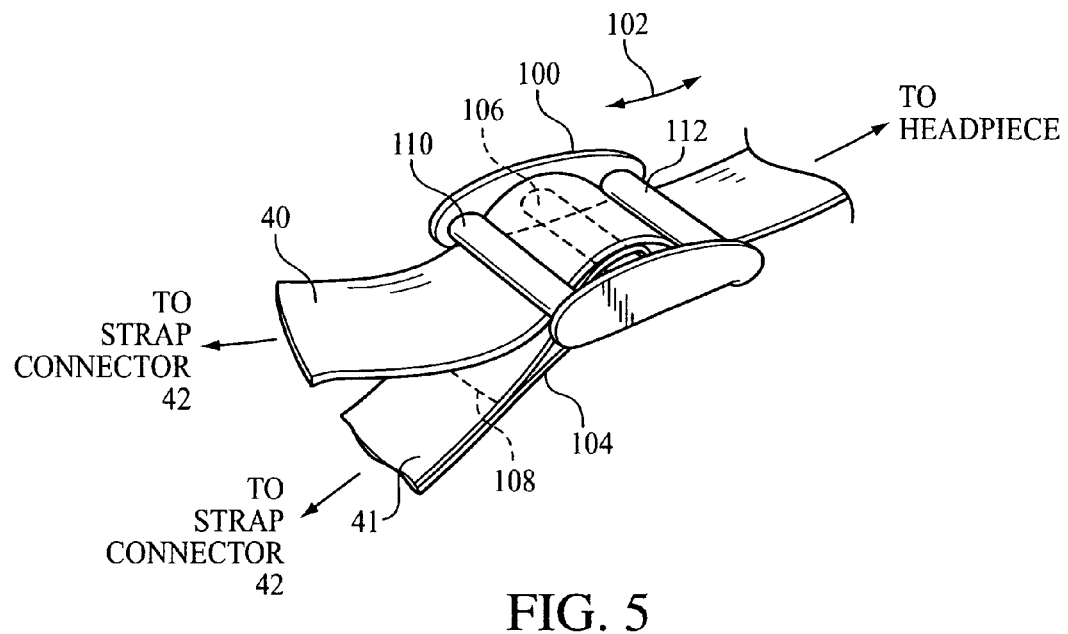
FIGS. 5 and 6 are perspective views of alternative designs for a headgear strap fastener clamp suitable for use with the headgear assembly of the present invention.
Figure 6:
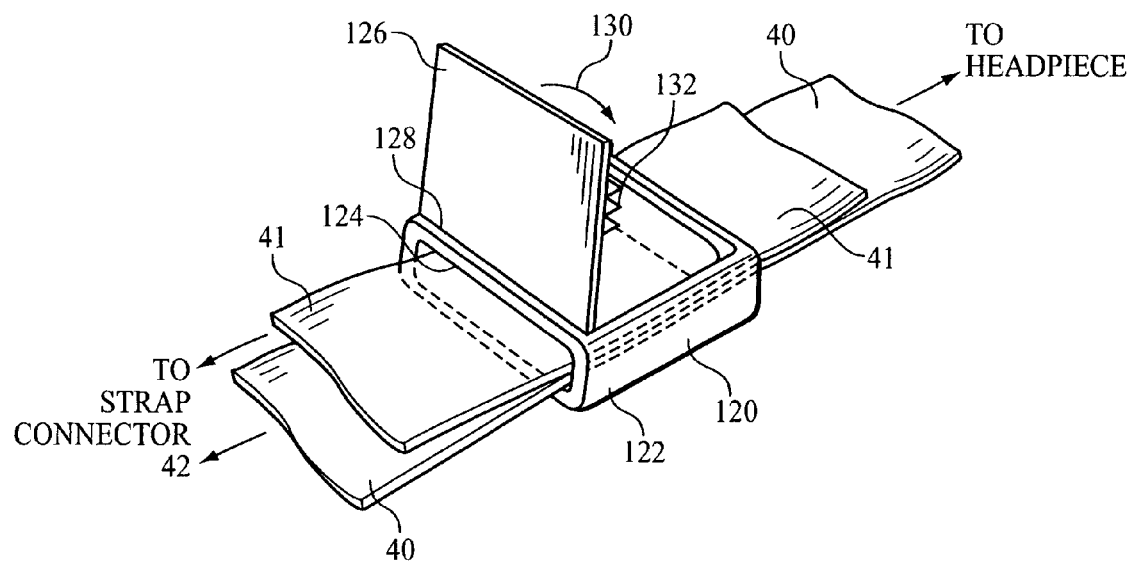

Two examples of locking clamps 100 and 120 that attach the end portion of the headgear strap to the rest of the strap are shown in FIGS. 5 and 6. Locking clamp 100 in FIG. 5 corresponds to a well known mechanism for attaching a free end of a strap to the remaining portions of the strap while allowing the position of the clamp relative to strap 40 to be moveable, as indicated by arrow 102. More specifically, a free end 104 of strap end portion 41 is secured to a center post 106 of clamp 100. For example, it is well know to stitch free end 104 to strap end portion 41, as indicated by dashed stitch line 108. Strap end portion 41 is threaded through strap connector 42 and then through posts 110 and 112 on clamp 100. In this manner, the length of the headgear strap from the headpiece to the strap connector can be adjusted and then maintained at the desired setting due to the binding effect of posts 108, 110 and 112 on the headgear strap.

Locking clamp 120 in FIG. 6 includes a body member 122 having a channel 124 defined therethrough so that the headgear straps 40 and 41 can pass through the body member. A clamping member 126 is attached to body member 122 via a hinge 128, such as a living hinge, so that the clamping member can close into an engaged relation with body member 122, as indicated by arrow 130. In the closed position (not shown), clamping member 126 pinches end portion 41 to a remaining portion of strap 40, thereby locking the strap in place. A free end portion 41a of strap 40 can be trimmed to remove excess length. Also, locking teeth 132 can be provided on clamp member 126. Although not illustrated, the present invention contemplates any conventional technique for securing clamp member 126 in the closed position, i.e., in an engaged relation with body member 122.

Referring again to FIGS. 1–4, strap connector 42 further includes a post portion 52 extending from the midpoint of the rigid elongated portion. In a preferred embodiment, post portion 52 is rigid. However, the present invention also contemplates that post portion 52 can be formed from a pliable or flexible material. At a distal end 54 of post portion 52, opposite elongated portion 48, is a bulbous portion 56 of a diameter that is larger, e.g., twice the diameter, of post portion 52. It can be appreciated that shapes other than the sphere shown in the figures are contemplated for bulbous portion 56.

To connect headgear straps 40 to mask 10, each post portion 52 is placed in a respective notch 36 on first connector 28. Small area 38 of reduced width provides a zone of interference between notch 36 and post portion 52, such that post portion 52 snaps in place in the notch. Bulbous portion 56, having a diameter larger than the notch width, maintains strap connector 42 within first connector 28. When strap connector 42 is placed in first connector 28, it is free to swivel a full 360 degrees about its axis, as well as rotate angularly through substantially 90 degrees of angular rotation about each of its other two axes. Once strap connector 42 and first connector 28 are engaged, the user is free to adjust and straighten the headgear straps 40, and lock the length of the strap at the desired setting as discussed above. Thereafter, the headgear can be easily disconnected from the mask by disengaging strap connector portion 56 from first connector 28.

In the illustrated exemplary embodiment of patient interface assembly 8, mask 10 includes a forehead support arm 51 to which is attached a forehead member 53. Forehead member 53 functions in the same manner as conventional forehead assemblies. Namely, it provides additional connections to which headgear straps 40 in headgear assembly 11 can be coupled to the forehead member. For example, in the embodiment illustrated in FIG. 1, headgear straps 40 are coupled to a snap element 55 that selectively engages forehead member 53 in any conventional manner. It can be appreciated, however, that the ball-and-socket configuration for first connector 28 and strap connector 42 can also be used in conjunction with forehead member 53 for selectively and rotateably attaching the headgear straps to the forehead member. Of course, snap element 55 can also be eliminated in favor of a more permanent attachment of the headgear strap to forehead member 53.

Alternative exemplary embodiments of the patient interface assembly of the present invention are illustrated in FIGS. 7–14. In these embodiment, many features are similar to those illustrated in FIGS. 1–4. It should be noted that the forehead assembly is not shown in these figures, because the relevant features and alternative configurations of the mask and headgear connector of the present invention can be garnered from the connection shown on the mask shell. However, the configurations for coupling the headgear to the mask shell shown in FIGS. 7–14 and described below are equally applicable to attaching the headgear to the forehead member or other similar forehead assembly.

Figure 7:
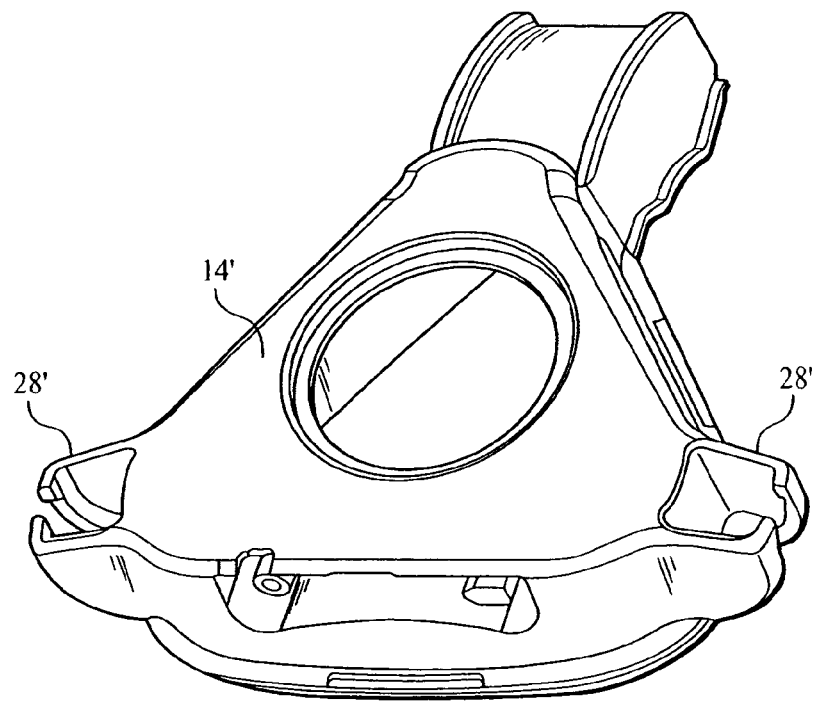
FIG. 7 is a perspective view of a second embodiment of a mask shell according to the principles of the present invention.
Figure 8:
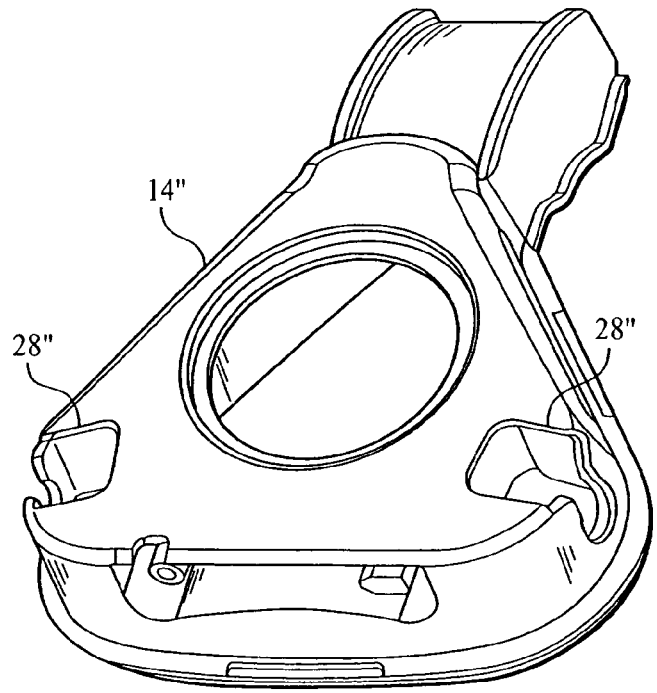
FIG. 8 is a perspective view of a third embodiment of a mask shell according to the principles of the present invention.
Figure 9:
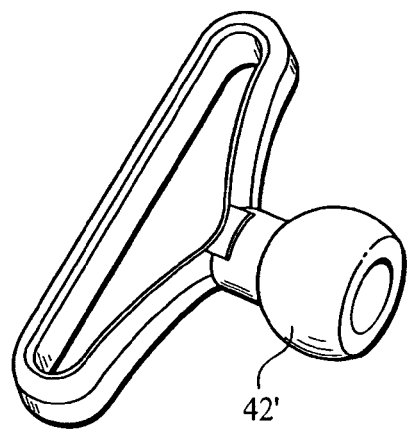
FIG. 9 is a perspective view of a second embodiment of a strap connector according to the principles of the present invention.
Figure 10:
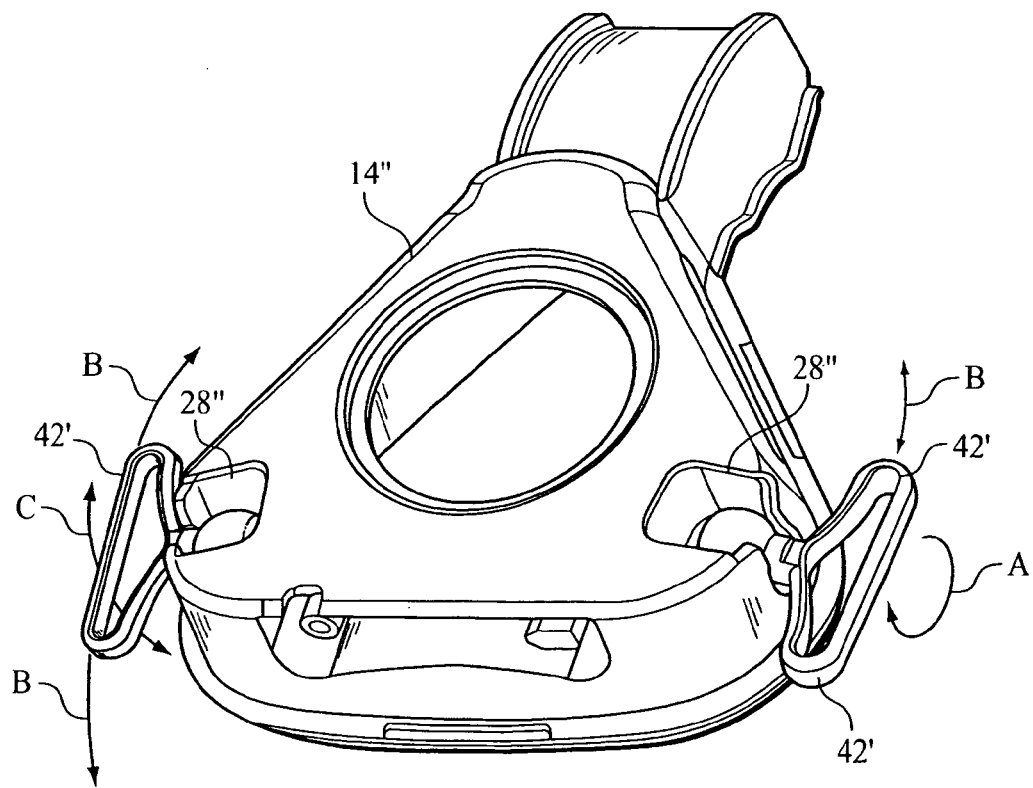
FIG. 10 is a perspective view of the mask shell shown in FIG. 9 and the strap connector shown in FIG. 8 illustrated in an engaged relation.
Figure 11:
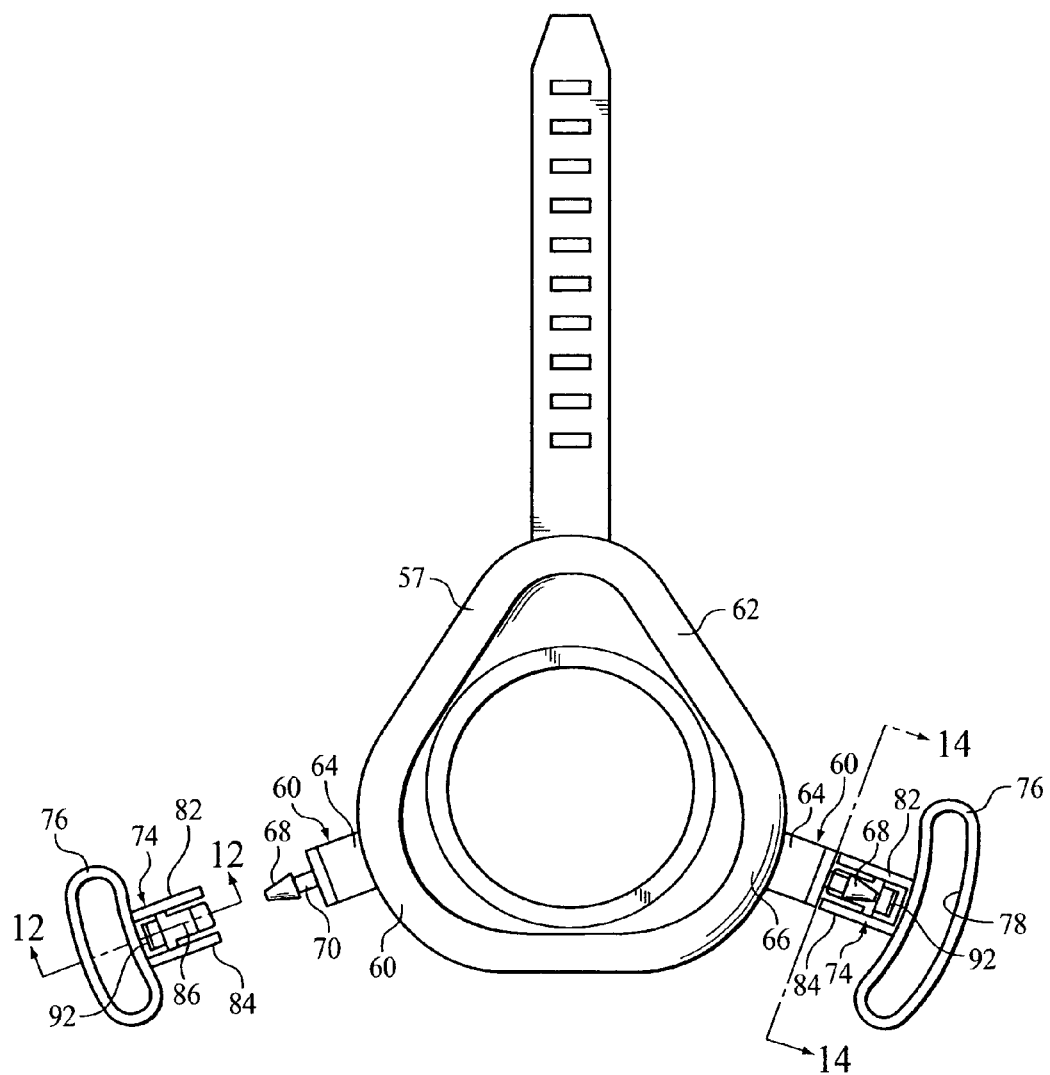
FIG. 11 is a partially exploded front view of a further embodiment of a patient interface assembly according to fourth embodiment of the present.
Figure 12:
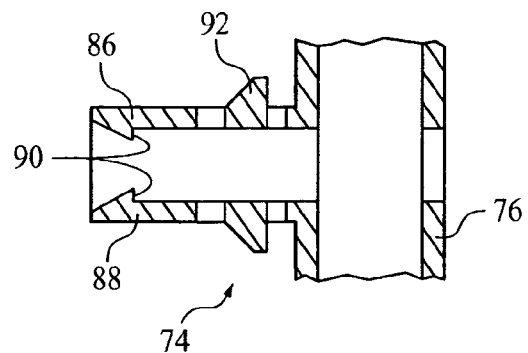
FIG. 12 is a cross-sectional view of the strap connector taken along line 12—12 in FIG. 11.
Figure 13:
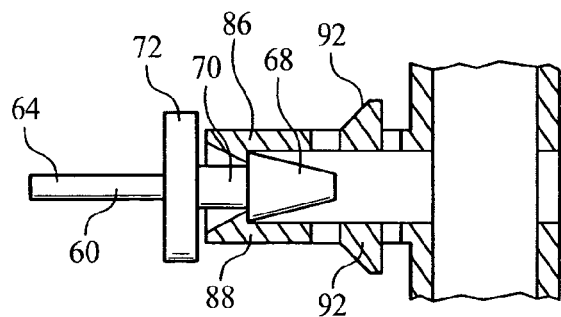
FIG. 13 is a partial cross-sectional view of a first connector connected to the strap connector in the mask assembly of FIG. 11.
Figure 14:
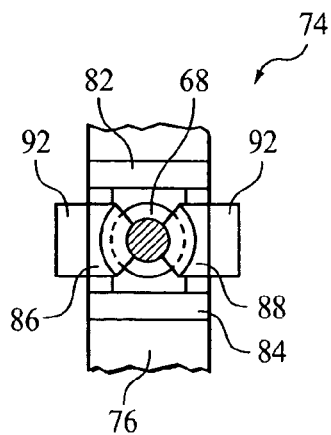
FIG. 14 is a cross-sectional view of the strap connector and first connector taken along line 14—14 of FIG. 11.

FIGS. 7 and 8 illustrate alternative embodiments for the mask shell, which are generally similar to mask shell 14 in FIGS. 1–3. However, mask shell 14' in FIG. 7 includes first connectors 28' that extend substantially perpendicularly from the lower angles 22' of the shell 14'. In the embodiment shown in FIG. 8, first connectors 28" are molded into mask shell 14", rather than protruding therefrom as in the previous embodiments. FIG. 9 illustrates an alternative embodiment for strap connector 42', and FIG. 10 shows how strap connectors 42 of FIG. 9 attach to mask shell 14" of FIG. 8 via first connectors 28". These alternative embodiments are provided to allow those skilled in the art to appreciate the variety of different configurations that are possible for first connectors 28, 28', 28" and strap connectors 42, 42' while still adhering to the basic principles of the present invention. These basic principles being to allow the strap connectors to 1) selectively attach to the mask shell, 2) rotate over a 360 degree angle, as illustrated by arrow A in FIG. 10, 3) move over a range of angles in a first plane that is generally parallel to that of mask shell 14, as indicated by arrow B, and 4) move over a range of angles in a second plane that is generally perpendicular to the plane of mask shell 14, as indicated by arrow C in FIG. 10.

A further alternative exemplary embodiment of the connection between a mask 57 and the headgear according to the principles of the present invention is illustrated in FIGS. 11–14. In this embodiment, each first connector 60 associated with mask shell 62 includes a first post portion 64 extending from each lower angle 66 of mask shell 62. At the distal end of first post portion 64, a cone-shaped member 68 extends from a second post portion 70. A retaining portion 72, having a diameter that is orientated generally perpendicular to first and second post portions 64 and 70, separates the first and second post portions. Retaining portion 72 forms a groove-like channel between the base of cone-shaped shaped member 68 and retaining portion 72.

In an exemplary embodiment of the present invention, first post portion 64 is a substantially planar portion so that it flexes in a direction perpendicular to the plane in which the mask shell is oriented and does not flex in a direction parallel to the plane in which the mask shell is oriented. It can be appreciated, however, that first post portion 64 can have any one of a variety of configurations, including being rigid and immovable. In addition, the present invention contemplates eliminating first post portion 64 entirely.

Each strap connector 74 includes a rigid elongated portion 76 having an elongated opening 78. The strap connector 70 further includes a third post portion 80 extending from the mid-point of elongated portion 76. Third post portion 76 includes two opposed rigid walls 82, 84 and two opposed flexing walls 86, 88 having internal semi-circular latching teeth 90 for engaging the groove formed at the base of cone-shaped member 68 of first connectors 60. The latching teeth 90 are releasable by pressing protrusions 92 on the outside of flexing walls 86 and 88.

Once latching teeth 90 engage with the groove on the first connector, it provides a secure connection that allows for a 360° rotation of the strap connector relative to the first connector. Additionally, the flexibility of the relatively thin post portion 70 allows for movement of the strap connector along two axis so that the strap connectors can provide a connection with the headgear straps that enable the straps to more closely conform to the facial contour of the user, i.e., do not protrude irregularly from the face of the user. It should be noted that the present invention contemplates that second post portion 70 can have any one of a variety of shapes and sizes to provide any desired range of flexing in any desired direction or directions.

In the illustrated embodiment, the first connectors are shown located at the lower sides of the mask shell. However, the present invention contemplates providing these connecting elements at other locations on the mask and oriented in any desired direction. For example, the first connector can be provided on the forehead assembly. The present invention also contemplates that the male-female orientation of the first connectors and strap connectors can be reversed. In other words, the ball element, which is shown in FIG. 1 as being on the strap connector, can be provided on the mask, and the socket element, which is shown in FIG. 1 as being on the first connector, can provided on the strap connector.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A gas delivery mask comprising:
   a shell for supporting a cushion, the cushion is configured to contact a patient and deliver a gas to the patient;
   a first connector associated with the shell;
   a second connector adapted to be connected to a headgear, wherein the headgear includes at least one strap adapted to secure the mask on a patient; and
   means for releasably connecting the first connector with the second connector such that the second connector is rotateable relative to the first connector in a plurality of axis of rotation simultaneously, whereby the first connector and the second connector interact to realeasably interconnect the shell with the headgear.

2. The gas delivery mask of claim 1, wherein the first connector is a female connector integrally formed with the shell and the second connector is a corresponding male connector.

3. The gas delivery mask of claim 2, wherein the first connector comprises a pair of a parallel walls and a curved notched wall abutting the parallel walls.

4. The gas delivery mask of claim 3, wherein the second connector comprises an elongated portion having an elongated opening adapted to receive a headgear strap.

5. The gas delivery mask of claim 4, wherein the second connector further comprises:
   a post portion having an axis and extending from the elongated portion; and
   a bulbous end portion associated with the distal end of the post portion, the bulbous end portion adapted for insertion in the notched wall of the first connector so as to permit 360 degrees of rotation about the axis of the post portion.

6. The gas delivery mask of claim 1, wherein the first connector is recessed with the shell and the first connector is a male connector integrally formed with the shell.

7. The gas delivery mask of claim 6, wherein the second connector is a corresponding female connector.

8. The gas delivery mask of claim 7, wherein the first connector comprises a flexible post portion, and a cone-shaped shaft associated with an end of the post portion.

9. The gas delivery mask of claim 8, wherein the second connector comprises an elongated portion having an opening adapted to receive a headgear strap.

10. The gas delivery mask of claim 9, wherein the second connector further comprises a post extending from the elongated portion and having opposed walls for rotateably receiving the cone-shaped shaft.

11. A gas delivery mask comprising:
    a shell for supporting a cushion, the cushion is configured to contact a patient and deliver a gas to the patient;
    a first connector associated with the shell;
    a second connector having a first portion that is configured and arranged so as to releasably connect to the first connector and a second portion that is adapted to connect to a headgear having at least one strap for securing the mask on a patient, and wherein the first connector and the second connector are configured and arranged such that the second connector is rotateable relative to the first connector in a plurality of axis of rotation simultaneously, whereby the first connector and the second connector interact to releasably interconnect the shell with the headgear.

12. The gas delivery mask of claim 11, wherein the first connector is a female connector integrally formed with the shell and wherein the second connector is a corresponding male connector.

13. The gas delivery mask of claim 12, wherein the first connector comprises a pair of a parallel walls and a notched wall abutting the parallel walls.

14. The gas delivery mask of claim 13, wherein the second connector comprises an elongated portion having an opening adapted to receive the strap.

15. The gas delivery mask of claim 14, wherein the second connector further comprises:
    a post portion having an axis and extending from the elongated portion; and
    a bulbous portion associated with a distal end of the post portion, the bulbous portion adapted for insertion in the notched wall of the first connector so as to permit 360 degrees of rotation about the axis of the post portion.

16. The gas delivery mask of claim 11, wherein the first connector is recessed with the shell.

17. The gas delivery mask of claim 11, wherein the first connector is a male connector integrally formed with the shell and the second connector is a corresponding female connector.

18. The gas delivery mask of claim 17, wherein the first connector comprises a flexible post portion, and a cone-shaped shaft associated with an end of the post portion.

19. The gas delivery mask of claim 18, wherein the second connector comprises an elongated portion having an opening adapted to receive the strap.

20. The gas delivery mask of claim 19, wherein the second connector further comprises a post extending from the elongated portion and having opposed walls for rotateably receiving the cone-shaped shaft.

21. A patient interface assembly comprising:
    (a) a gas delivery mask comprising:
       (1) a shell for supporting a cushion, the cushion is configured to contact a patient and deliver a gas to the patient,
       (2) a first connector associated with the shell, and
       (3) a second connector releasably connected to the first connector, and wherein the first connector and the second connector are configured and arranged such that the second connector is rotateable relative to the first connector in a plurality of axis of rotation simultaneously; and (b) a headgear adapted for securing the mask on a patient comprising a connecting strap adapted to connect the headgear to the second connector, whereby the first connector and the second connector interact to realeasably interconnect the shell with the headgear.

22. The patient interface assembly of claim 21, wherein the first connector is a female connector integrally formed with the shell and the second connector is a corresponding male connector.

23. The patient interface assembly of claim 22, wherein the first connector comprises a pair of a parallel walls and a notched wall abutting the parallel walls.

24. The patient interface assembly of claim 23, wherein the second connector comprises an elongated portion having an opening adapted to receive the strap.

25. The patient interface assembly of claim 24, wherein the second connector further comprises:
a post portion having an axis and extending from the elongated portion; and
a bulbous portion associated with an end of the post portion, the bulbous portion adapted for insertion in the notched wall of the first connector so as to permit 360 degrees of rotation about the axis of the post portion.

26. The patient interface assembly of claim 21, wherein the first connector is a male connector integrally formed with the shell and the second connector is a corresponding female connector.

27. The patient interface assembly of claim 26, wherein the first connector comprises a flexible post portion, and a cone-shaped shaft associated with an end of the post portion.

28. The patient interface assembly of claim 27, wherein the second connector comprises an elongated portion having an opening adapted for receiving the strap.

29. The patient interface assembly of claim 28, wherein the second connector further comprises a post extending from the elongated portion and having opposed walls for rotateably receiving the cone-shaped shaft.

30. The patient interface assembly of claim 21, further comprising a locking clamp coupled to the connecting strap.

31. A system for delivering a breathing gas to a patient comprising:
(a) a gas flow generating device that produces a flow of gas;
(b) a conduit having a first end portion operatively coupled to the gas flow generating device and a second end portion, wherein the conduit is adapted to carry the flow of gas from the gas flow generating device during operation of the system;
(c) a gas delivery mask comprising:
(1) a shell for supporting a cushion, the cushion is configured to contact a patient and deliver the gas to the patient,
(2) a first connector associated with the shell, and
(3) a second connector releasably connected to the first connector and wherein the first connector and the second connector are configured and arranged such that the second connector is rotateable relative to the first connector in a plurality of axis of rotation simultaneously, and
(d) a headgear adapted to secure the mask on a patient, comprising:
a connecting strap adapted to connect the headgear to the second connector of the gas delivery mask, whereby the first connector and the second connector interact to realeasably interconnect the shell with the headgear.

32. The system of claim 31, wherein the first connector is a female connector integrally formed with the shell and the second connector is a corresponding male connector.

33. The gas delivery mask of claim 32, wherein the first connector comprises a pair of a parallel walls and a notched wall abutting ends of the parallel walls.

34. The system of claim 33, wherein the second connector comprises an elongated portion having an opening adapted to receive the strap.

35. The system of claim 34, wherein the second connector further comprises:
a post portion extending from the elongated portion; and
a bulbous portion associated with an end of the post portion, wherein the bulbous portion is adapted for insertion in the notched wall of the first connector.

36. The system of claim 31, wherein the first connector is a male connector integrally formed with the shell and the second connector is a corresponding female connector.

37. The system of claim 36, wherein the first connector comprises a flexible post portion, and a cone-shaped shaft associated with an end of the post portion.

38. The system of claim 37, wherein the second connector comprises an elongated portion having an opening adapted to receive the strap.

39. The system of claim 38, wherein the second connector further comprises a post extending from the elongated portion and having opposed walls for rotateably receiving the cone-shaped shaft.

40. The system of claim 31, further comprising a locking clamp coupled to the connecting strap.

41. The system of claim 31, wherein the gas delivery mask is a nasal mask or a nasal/oral face mask.

42. The gas delivery mask of claim 1, wherein the plurality of axis of rotation comprise three axis of rotation.

43. The gas delivery mask of claim 11, wherein the plurality of axis of rotation comprise three axis of rotation.

44. The gas delivery mask of claim 21, wherein the plurality of axis of rotation comprise three axis of rotation.

45. The gas delivery mask of claim 31, wherein the plurality of axis of rotation comprise three axis of rotation.

* * * * *